United States Patent [19]

Cassar et al.

[11] Patent Number: 4,613,669
[45] Date of Patent: Sep. 23, 1986

[54] PREPARATION OF 1,4-DIKETOPYRROLO-[3,4-C]PYRROLES

[75] Inventors: Luigi Cassar, Bologna, Italy; Abul Iqbal, Ettingen; Alain C. Rochat, Fribourg, both of Switzerland

[73] Assignee: Ciba-Geigy Corporation, Ardsley, N.Y.

[21] Appl. No.: 512,074

[22] Filed: Jul. 8, 1983

[30] Foreign Application Priority Data

Jul. 8, 1982 [CH] Switzerland .................. 4171/82

[51] Int. Cl.$^4$ ............... C07D 487/04; C07D 403/14; C07D 407/14; C07D 409/14
[52] U.S. Cl. ............................ 546/167; 546/272; 548/453
[58] Field of Search ............... 548/453; 546/272, 167

[56] References Cited

FOREIGN PATENT DOCUMENTS 61426  3/1982  European Pat. Off. ............ 207/26

OTHER PUBLICATIONS

Kagan et al., Bulletin de la Societe Chimique de France 1819–1822, (1966).
Arsenijevic et al., Bulletin de la Societe Chimique de France 3403–3408, (1968).
Santaniello et al., Synthesis 698 (Oct. 1977).
Iimori et al., Tetrahedron Letters, 27, 2525–2528 (1979).
Dardoize et al., Bulletin de la Societe Chimique de France 3841–3846, (1972).
Farnum et al., Tetrahedron Letters 29, 2549–2552, (1974).

Primary Examiner—Richard L. Raymond
Assistant Examiner—D. B. Springer
Attorney, Agent, or Firm—Harry Falber

[57] ABSTRACT

A process for the preparation of 1,4-diketopyrrolo-[3,4-c]pyrroles of the formula

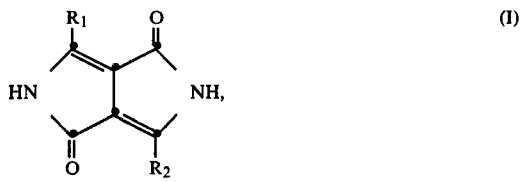

(I)

wherein each of $R_1$ and $R_2$ independently of the other is an isocyclic aromatic or non-basic heterocyclic aromatic radical, which process comprises reacting 1 mole of the compound of formula

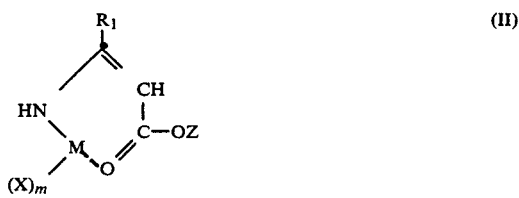

(II)

wherein M is a metal atom, Z is alkyl or aryl, X is halogen or acetate, and m is a value from 0 to 2, with 1 mole of a compound of the formula $$YCH_2COOZ \quad \text{(III)}$$

wherein Y is halogen, and with 1 mole of a nitrile of the formula $$R_1\text{—CN} \quad \text{(IV) or } R_2\text{—CN} \quad \text{(V)}$$

in an organic solvent and at elevated temperature, and isolating the compound of formula I.

The compounds obtained according to the invention are suitable for pigmenting organic material of high molecular weight.

8 Claims, No Drawings

PREPARATION OF 1,4-DIKETOPYRROLO-[3,4-C]PYRROLES

The present invention relates to a process for the preparation of 1,4-diketopyrrolo[3,4-c]pyrroles which are valuable pigments. A process for the preparation of 1,4-diketo-3,6-diphenylpyrrolo[3,4-c]pyrrole starting from benzonitrile and ethyl bromoacetate in the presence of activated zinc-copper couple is described in Tetrahedron Lett. 1974, 2549-52. However, the yields obtained up to now have been unsatisfactory. By using the compounds of this invention as starting materials, the desired pyrrolo[3,4-c]-pyrrole pigments are obtained in substantially higher yield and purity. Moreover, it is possible by means of the process of this invention selectively to obtain homogeneously asymmetrical 1,4-diketopyrrolo[3,4-c]pyrroles. In addition, it is all the more surprising that the desired pigments are obtained with the combination of starting materials of this invention, as according to Tetrahedron Lett. 1974, 2459-52, the compounds of formula II are presumed to dimerise and not to be able to react with the other two components.

Accordingly, the present invention provides a process for the preparation of 1,4-diketopyrrolo[3,4-c]pyrroles of the formula

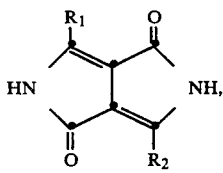

wherein each of $R_1$ and $R_2$ independently of the other is an isocyclic aromatic or non-basic heterocyclic aromatic radical, which process comprises reacting 1 mole of the compound of formula

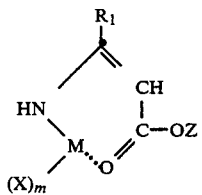

wherein M is a metal atom, Z is alkyl or aryl, X is halogen or acetate, and m is a value from 0 to 2, with 1 mole of a compound of the formula $$YCH_2COOZ \qquad (III)$$

wherein Y is halogen, and with 1 mole of a nitrile of the formula $$R_1\text{—}CN \qquad (IV)$$

or $$R_2\text{—}CN \qquad (V)$$

in an organic solvent and at elevated temperature, and isolating the compound of formula I.

The radicals $R_1$ and $R_2$ may be different or identical. $R_1$ and $R_2$ as isocyclic aromatic radicals are preferably monocyclic to tetracyclic radicals, most preferably monocyclic or bicyclic radicals, i.e. phenyl, diphenylyl or naphthyl. Non-basic heterocyclic aromatic radicals $R_1$ and $R_2$ are preferably monocyclic to tricyclic radicals. These radicals may be entirely heterocyclic or may contain a heterocyclic ring and one or more fused benzene rings, e.g. thienyl, furoyl, thiophenyl, coumarinyl or benzfuranyl.

Both the isocyclic and the heterocyclic aromatic radicals may contain the customary non-watersolubilising substituents such as:

(1) Halogen atoms, e.g. chlorine, bromine or fluorine atoms.

(2) Branched or unbranched alkyl groups containing preferably 1 to 18, especially 1 to 12, more particularly 1 to 8 and, most preferably, 1 to 4, carbon atoms. These alkyl groups may contain non-watersolubilising substituents, e.g. fluorine, hydroxyl, cyano, —$OCOR_3$, —$OR_4$, —$COOR_3$, —$CONR_4R_5$ or —$R_3$—$OCONHR_3$, wherein $R_3$ is alkyl, aryl such as naphthyl, or benzyl or benzyl substituted by halogen, alkyl or —O-alkyl, or is a heterocyclic radical; $R_4$ and $R_5$ are hydrogen, alkyl or alkyl substituted by cyano or hydroxy, or is $C_5$–$C_6$cycloalkyl, aryl or heteroaryl, especially phenyl or phenyl substituted by halogen, alkyl or —O-alkyl, or wherein $R_4$ and $R_5$ together with the nitrogen atom form a 5- or 6-membered heterocyclic ring, e.g. a morpholine, piperidine or phthalimide ring. Further possible substituents at the alkyl groups or mono- or dialkylated amino groups, aryl radicals such as naphthyl or preferably phenyl or phenyl substituted by halogen, alkyl or —O-alkyl, or also non-basic heterocyclic aromatic radicals such as 2-thienyl or 6-benzimidazolonyl radicals.

If the substituents specified in (2) above in turn contain alkyl, then this alkyl moiety may be branched or unbranched and contain preferably 1 to 18, especially 1 to 12, more particularly 1 to 8 and, most preferably, 1 to 4 carbon atoms.

Examples of unsubstituted or substituted alkyl groups are: methyl, ethyl, n-propyl, isopropyl, n-butyl, sec-butyl, tert-butyl, tert-amyl, n-pentyl, n-hexyl, 1,1,3,3-tetramethylbutyl, n-heptyl, n-octyl, nonyl, decyl, undecyl, dodecyl, hydroxymethyl, trifluoromethyl, trifluoroethyl, cyanomethyl, methoxycarbonylmethyl, acetoxymethyl or benzyl.

(3) The —$OR_6$ group, wherein $R_6$ is hydrogen, alkyl, or aryl such as naphthyl or preferably phenyl or phenyl substituted by halogen, alkyl or —O-alkyl, or is $C_5$–$C_6$-cycloalkyl, aralkyl or a non-basic heterocyclic radical. In the definition of $R_6$, alkyl may contain a number of carbon atoms specified as preferred in (2) above. Typical examples of $R_6$ are: methyl, ethyl, n-propyl, isopropyl, trifluoroethyl, phenyl, o-, m- or p-chlorophenyl, o-, m- or p-methylphenyl, α- or β-naphthyl, cyclohexyl, benzyl, thienyl or pyranylmethyl.

(4) The —$SR_6$ group, wherein $R_6$ is as defined in (3) above. Typical examples of $R_6$ are: methyl, ethyl, n-propyl, isopropyl, phenyl, o-, m- or p-chlorophenyl, o-, m- or p-methylphenyl, α- or β-naphthyl, cyclohexyl, benzyl, thienyl or pyranylmethyl.

(5) The cyano group.

(6) The group of the formula —$COOR_3$, wherein $R_3$ is as defined in (2). Examples of $R_3$ are: methyl, ethyl, isopropyl, tert-butyl, n-butyl, phenyl, benzyl or furfuryl.

(7) The group of the formula —$COR_6$, wherein $R_6$ is as defined in (3). Examples of $R_6$ are: methyl, ethyl, tert-butyl, phenyl, o-, m- or p-chlorophenyl, o-, m- or p-methylphenyl or α- or β-naphthyl.

(8) The group of the formula —NR$_7$COR$_3$, wherein R$_3$ is as defined in (2). R$_7$ is hydrogen, alkyl, aryl, e.g. naphthyl or preferably phenyl or phenyl substituted by halogen, alkyl or —O-alkyl, or is C$_5$–C$_6$cycloalkyl, aralkyl or the radical —COR$_3$, with two radicals —COR$_3$ together with the nitrogen atom being able to form a heterocyclic ring. In the definition of R$_7$, alkyl may contain a number of carbon atoms specified as preferred in (2) above. Typical examples are: acetylamino, propionylamino, butyrylamino, benzoylamino, p-chlorobenzoylamino, p-methylbenzoylamino, N-methylacetylamino, N-methylbenzoylamino, N-succinimido or N-phthalimido.

(9) The group of the formula —NR$_6$COOR$_3$, wherein R$_3$ and R$_6$ are as defined in (2) and (3) respectively. Typical examples are the —NHCOOCH$_3$, NHCOOC$_2$H$_5$ or NHCOOC$_6$H$_5$ groups.

(10) The group of the formula —NR$_6$CONR$_4$R$_5$, wherein R$_6$, R$_5$ and R$_4$ are as defined in (3) and (2). Typical examples are: ureido, N-methylureido, N-phenylureido or N,N-2',4'-dimethylphenylureido.

(11) The group of the formula —NHSO$_2$R$_3$, wherein R$_3$ is as defined in (3). Typical examples are: methanesulfonylamino, phenylsulfonylamino, p-toluylsulfonylamino or β-naphthylsulfonylamino.

(12) The groups of the formula —SO$_2$R$_3$ or SOR$_3$, wherein R$_3$ is as defined in (2) above. Typical examples are: methylsulfonyl, ethylsulfonyl, phenylsulfonyl, 2-naphthylsulfonyl, phenylsulfoxidyl.

(13) The group of the formula —SO$_2$OR$_3$, wherein R$_3$ is as defined in (2) above. Typical examples of R$_3$ are: methyl, ethyl, phenyl, o-, m- or p-chlorophenyl, o-, m- or p-methylphenyl, α- or β-naphthyl.

(14) The group of the formula —CONR$_4$R$_5$, wherein R$_4$ and R$_5$ are as defined in (2). Examples of R$_4$ and R$_5$ are: carbamoyl, N-methylcarbamoyl, N-ethylcarbamoyl, N-phenylcarbamoyl, N,N-dimethylcarbamoyl, N-methyl-N-phenylcarbamoyl, N-α-naphthylcarbamoyl or N-piperidylcarbamoyl.

(15) The group of the formula —SO$_2$NR$_4$R$_5$, wherein R$_4$ and R$_5$ are as defined in (2) above. Typical examples are: sulfamoyl, N-methylsulfamoyl, N-ethylsulfamoyl, N-phenylsulfamoyl, N-methyl-N-phenylsulfamoyl or N-morpholylsulfamoyl.

(16) The group of the formula —N=N—R$_8$, wherein R$_8$ is the radical of a coupling component or is a phenyl radical which is unsubstituted or substituted by halogen, alkyl or O-alkyl. In the definition of R$_8$, alkyl may contain a number of carbon atoms specified in (2) as preferred. Examples of R$_8$ are: acetoacetarylide, pyrazolyl, pyridonyl, o- or p-hydroxyphenyl, o-hydroxynaphthyl, p-aminophenyl or p-N,N-dimethylaminophenyl radicals.

(17) The group of the formula —OCOR$_3$, wherein R$_3$ is as defined in (2) above. Examples of R$_3$ are: methyl, ethyl, phenyl, o-, m- or p-chlorophenyl.

(18) The group of the formula —OCONHR$_3$, wherein R$_3$ is as defined in (2) above. Examples of R$_3$ are: methyl, ethyl, phenyl, o-, m- or p-chlorophenyl.

X and Y as halogen in the compounds of the formulae II and III may be chlorine, bromine or iodine.

Alkyl groups Z in the compounds of the formulae II and III can be branched or unbranched and contain preferably 1 to 12, in particular 1 to 8 and, most preferably, 1 to 5 carbon atoms. Examples of such alkyl groups are: methyl, ethyl, n-propyl, isopropyl, n-butyl, sec-butyl, tert-butyl, n-pentyl, tert-amyl, n-hexyl, n-heptyl, n-octyl and 1,1,3,3-tetramethylbutyl.

Z as aryl in the compounds of the formulae II and III is preferably unsubstituted phenyl or phenyl substituted by halogen such as chlorine, or C$_1$–C$_6$ alkyl such as methyl, ethyl, isopropyl or tert-butyl, or C$_1$–C$_6$alkoxy such as methoxy or ethoxy. Aryl is preferably unsubstituted phenyl.

M as metal atom in the compounds of the formula II can be in particular a monovalent, bivalent or trivalent metal atom, e.g. lithium, sodium, potassium, magnesium, calcium, zinc, copper or aluminium. The preferred metal atom is zinc.

In the process of this invention, the preferred starting materials are compounds of the formula II, wherein R$_1$ is unsubstituted phenyl or naphthyl or phenyl or naphthyl which contain non-watersolubilising substituents.

More preferred starting materials are compounds of the formula II, wherein R$_1$ is the radical of the formula VI

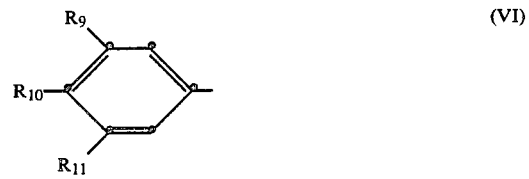

wherein each of R$_9$, R$_{10}$ and R$_{11}$ independently of one another is hydrogen, halogen, carbamoyl, cyano, trifluoromethyl, C$_2$–C$_{13}$alkylcarbamoyl, C$_1$–C$_{12}$alkyl, C$_1$–C$_{12}$alkoxy, C$_1$–C$_{12}$alkylmercapto, C$_2$–C$_{13}$alkoxycarbonyl, C$_2$–C$_{13}$alkanoylamino or phenoxy, phenylmercapto, phenoxycarbonyl, phenylcarbamoyl or benzoylamino, each unsubstituted or substituted by halogen, C$_1$–C$_{12}$alkyl or C$_1$–C$_{12}$alkoxy, with the proviso that at least one of R$_9$, R$_{10}$ and R$_{11}$ is hydrogen.

In particular, preferred starting materials are compounds of the formula II, wherein R$_1$ is the radical of the formula VII

wherein one of R$_{12}$ and R$_{13}$ is chlorine, bromine, C$_1$–C$_4$alkyl, cyano, C$_1$–C$_4$alkoxy, or is phenoxy, carbamoyl or C$_2$–C$_5$alkylcarbamoyl, each unsubstituted or substituted by chlorine or methyl, or is phenylcarbamoyl which is unsubstituted or substituted by chlorine, methyl or methoxy, and the other is hydrogen.

In preferred starting materials of the formula II, X is bromine or chlorine, M is sodium, potassium, magnesium or zinc, m is 0 or 1, and Z is C$_1$–C$_8$alkyl.

In particularly preferred compounds of the formula II, X is bromine, M is zinc, m is 1, and Z is C$_1$–C$_5$alkyl.

In preferred starting materials of the formula III, Y is bromine or chlorine and Z is C$_1$–C$_8$alkyl, preferably C$_1$–C$_5$alkyl. It is most preferred to use methyl bromoacetate or ethyl bromoacetate.

Nitriles preferably used as compounds of the formula IV and V in the process of this invention are those in which R$_1$ and R$_2$ are unsubstituted phenyl or naphthyl or phenyl or naphthyl which carry non-water-solubilising substituents. It is most preferred to use nitriles of the formulae IV and V in which $R_1$ and $R_2$ are radicals of the formula VI, preferably of formula VII.

As starting materials, it is advantageous to use compounds of the formulae II and V, wherein $R_1$ and $R_2$ are different from each other.

The reaction of the compounds of formulae II and III with the compound of formulae IV and V is carried out in an organic solvent. Examples of suitable solvents are ethers such as tetrahydrofuran, dioxan, anisole or diphenyl ethers, or glycol ethers such as ethylene glycol dimethyl ether, ethylene glycol diethyl ether, diethylene glycol dimethyl ether or diethylene glycol diethyl ether; as well as dipolar aprotic solvents such as dimethylformamide, N,N-dimethylacetamide, nitrobenzene, N-methylpyrrolidone; aliphatic or aromatic hydrocarbons or mixtures thereof such as benzene or benzene substituted by alkyl or halogen, e.g. toluene, xylene, trimethylbenzene, isopropylbenzene or chlorobenzenes. In addition, it is also possible to use the nitrile of the formula IV or V as solvent if it is liquid in the temperature range in which the reaction takes place. Mixtures of the above solvents may also be used. It is convenient to use 5 to 20 parts by weight of solvent per 1 part by weight of the total amount of the reactants.

In the process of the invention it is preferred to use an ether or an aromatic hydrocarbon as solvent, in particular ethylene glycol dimethyl ether, tetrahydrofuran, dioxan, anisole, toluene, o-, m- or p-xylene, trimethylbenzene or isopropylbenzene.

The process of the invention is preferably carried out in the temperature range from 60° to 160° C., preferably from 90° to 140° C.

The compound of formula I can be isolated by filtration. This is conveniently done by diluting the reaction solution, before filtration, with an organic solvent, e.g. acetone, and washing the compound of formula I with water after filtration. In addition to the water used for washing it is possible to employ an inorganic or organic acid, e.g. hydrochloric acid or acetic acid.

In the process for the preparation of the compounds of formula I, it is in principle possible to charge the reaction vessel, at low temperature, with all the components and then to heat the mixture to the range of the reaction temperature, or to add the individual components, in any order, to each other in the range of the reaction temperature. A preferred embodiment of the reaction, which usually has a particularly advantageous influence on the yield, consists in charging the reaction vessel with the compound of formula II together with the aromatic nitrile of the formula IV or V and then adding the compound of formula III in the range of the reaction temperature. It is entirely possible to carry out the process of the invention not only batchwise, but also continuously. Although it usually suffices to employ stoichiometric amounts of the reactants, the yield can be improved by using in particular an excess of up to about 2.5 moles of the compound of formula IV or V per mole of compound of the formula II.

The process of this invention makes it possible to obtain compounds of formula I, wherein $R_1$ and $R_2$ are different, with excellent selectivity.

The compounds of the formulae III, IV and V are known or they may be prepared by methods which are known per se.

The compounds of formula II can be obtained by reacting a compound of the formula VIII

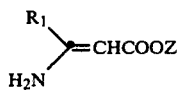

(VIII)

wherein $R_1$ and Z are as defined above, with a metal M or metal salt $MX_m$, wherein M, X and m are as defined above, under conditions which are known per se. The compounds of formula VIII can in turn be prepared by different known methods, for example by reacting cyanoacetates with organometal compounds of the $R_1MgX$ type, wherein X is halogen.

Depending on the nature of their substituents and on the polymers to be coloured, the compounds of formula I may also be used as polymer-soluble colourants. Normally, however, the compounds of formula I are used as pigments for organic materials of high molecular weight and can be used in general direct in the form in which they are obtained by the process of this invention.

Depending on the end use, the pigments obtained by the process of the invention can be converted into a more opaque or more transparent form.

It is possible first to isolate the pigment after the hydrolysis and then to heat it in water or an organic solvent, with or without pressure, in order to obtain the opaque form. It is preferred to employ an organic solvent having a boiling point above 80° C. Particularly suitable solvents are benzenes which are substituted by halogen atoms or by alkyl or nitro groups, e.g. xylenes, chlorobenzene, o-dichlorobenzene or nitrobenzene, as well as pyridine bases such as pyridine, picoline or quinoline, and also ketones such as cyclohexanone, ethers such as ethylene glycol monomethyl or monoethyl ether, amides such as dimethylformamide or N-methylpyrrolidone, and also dimethylsulfoxide or sulfolane. The aftertreatment may also be carried out in water in the presence of an organic solvent and/or with the addition of surface-active compounds.

Organic materials of high molecular weight which may be pigmented with the compounds of formula I are e.g. cellulose ethers and esters such as ethyl cellulose, nitrocellulose, cellulose acetate, cellulose butylate, natural resins or synthetic resins such as polymerisation resins or condensation resins, e.g. aminoplasts, in particular urea/formaldehyde and melamine/formaldehyde resins, alkyd resins, phenolic plastics, polycarbonates, polyolefins such as polystyrene, polyvinyl chloride, polyethylene, polypropylene, polyacrylonitrile, polyacrylates, polyamides, polyurethanes or polyesters, rubber, casein, silicone and silicone resins, individually or in mixtures.

It is immaterial whether the above organic compounds of high molecular weight are in the form of plastics, melts or of spinning solutions, lacquers, paints or printing inks. Depending on the end use, it is advantageous to use the pigments of this invention in the form of toners or formulations. The compounds of the formula I are employed in an amount of preferably 0.1 to 10% by weight, based on the organic material of high molecular weight to be pigmented.

The colorations obtained, e.g. in plastics, filaments, lacquers or printing inks, have excellent tinctorial strength, good dispersibility, good fastness to overspraying, migration, heat, light and atmospheric influences, as well as good gloss.

The invention is illustrated by the following Examples. Percents are percents by weight.

EXAMPLE 1

A solution of 9.3 g (0.05 mole) of allylzinc bromide in 150 ml of tetrahydrofuran is added to a solution of 9.55 g (0,05 mole) of ethyl β-aminocinnamate in 50 ml of tetrahydrofuran and the mixture is reacted for 3 hours at 10° C. The solvent is then distilled off in vacuo, affording the salt of formula IX

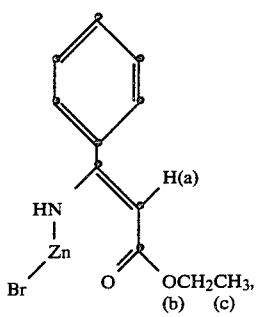
(IX)

which is characterised by $^1$H-NMR spectroscopy in CD$_3$CN in a 250 MHz Bruker NMR spectrophotometer and indicates the following values for the chemical shifts: δ(a) 5.14 ppm, δ(b) 4.26 ppm, δ(c) 1.23 ppm.

The salt of formula IX is dissolved in 50 ml of benzonitrile and to this solution are added 8.35 g (0.05 mole) of ethyl bromoacetate. The mixture is stirred for 8 hours at 120° C., then the red suspension is cooled, diluted with 50 ml of acetone, and stirred for another 10 minutes. The batch is filtered and the residue is washed with acetone and purified by boiling it in 25 ml of glacial acetic acid for 4 hours at reflux temperature. The product is isolated by filtration, washed once more with acetone and dried at 80° C. in vacuo, affording 3.2 g (22% of theory, based on ethyl bromoacetate) of pure pigment of the formula X

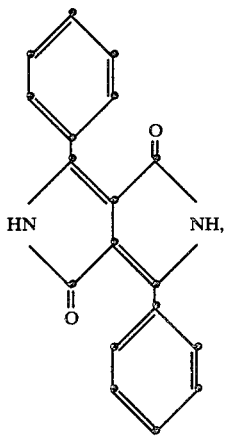
(X)

which colours PVC red.

Microanalysis: C$_{18}$H$_{12}$N$_2$O$_2$: MG 288.3: cal.: C 74.99%; H 4.22%; N 9.72%; found: C 74.70%; H 4.40%; N 9.85%

EXAMPLE 2

0.8 g of Cu(OCOCH$_3$)$_2$.H$_2$O are dissolved in 25 ml of glacial acetic acid at 90° C. and to the solution are added 14.4 g (0.22 mole) of zinc dust. The mixture is stirred for 1 minute, decanted, and the zinc is washed with glacial acetic acid and benzonitrile. The activated zinc, which still contains 9 ml of benzonitrile, is added to 50 ml (0.5 mole) of benzonitrile and then 0.05 g of iodine are added. Then 1 ml (0.2 mole) of ethyl bromoacetate is added dropwise, under nitrogen, over 1 hour at 20° C. When the dropwise addition is complete, the mixture is stirred for 12 hours at 20° C. $^1$H-NMR spectroscopy and gas chromatography show that the ethyl bromoacetate is completely reacted and that the mixture contains 0.2 mole (67.0 g) of the salt of formula IX.

To this mixture containing the salt of formula IX are added 100 ml of xylene and 22.1 ml (0.2 mole) of ethyl bromoacetate. After stirring for 10 hours at 130° C., the red suspension is cooled, diluted with acetone and filtered. The residue is washed with acetone, boiled in glacial acetic acid, collected once more by filtration and washed with acetone and dried in vacuo, affording 12.5 g (43% of theory, based on the salt of formula IX) of the pigment of formula X. 45 g of benzonitrile and 16 g of ethyl bromoacetate are recovered by distillation of the filtrate. The yield of pigment of formula X is 63% based on reacted benzonitrile, and 28% based on reacted ethyl bromoacetate.

EXAMPLE 3

5.1 g of a 45% dispersion of sodium are added to 100 ml of xylene and to the mixture is added a solution of 17.7 g of methyl β-aminocinnamate in 100 ml of xylene. The mixture is heated to 60°-70° C. and stirred for 30 minutes at this temperature, then cooled to room temperature. 22.5 g of zinc bromide are added and the mixture is stirred for 30 minutes at 40° C. To the zinc salt of methyl β-aminocinnamate so prepared in situ is added a mixture of 11.1 ml of methyl bromoacetate and 10.3 ml of benzonitrile. The yellow suspension so obtained is heated to 110° C. and stirred at this temperature for 15 hours. 40 ml of glacial acetic acid are then added and the reaction mixture is stirred for 15 minutes at 100° C. The reaction mixture is cooled to 80° C., 200 ml of acetone are stirred in, and the precipitate is isolated by filtration, washed with acetone and dried in vacuo at 80° C. Elemental analysis shows that the resultant red powder is identical with the pigment of formula X obtained in Example 1.

EXAMPLE 4

Following the procedure of Example 1, the salt of formula XI

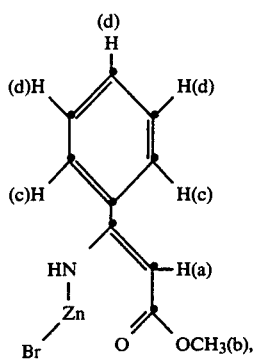
(XI)

is prepared from 9.3 g (0.05 mole) of allylzinc bromide and 8.35 g (0.05 mole) of methyl β-aminocinnamate. The product is characterised by ¹H-NMR spectroscopy in CD₃CN using a 250 MHz Bruker NMR spectrophotometer:

δ(a) 4.88 ppm (s), δ(b) 3.63 ppm (s), δ(c) 7.59 ppm (m), δ(d) 7.46 ppm (m).

The salt of formula XI is suspended in 30 ml of xylene and to the suspension are added 8.35 g (0.05 mole) of methyl bromoacetate and 15.5 g (0.113 mole) of p-chlorobenzonitrile. The mixture is stirred for 8 hours at 120° C. Working up as in Example 1 yields 4.2 g (26% of theory, based on methyl bromoacetate) of the pigment of formula XII

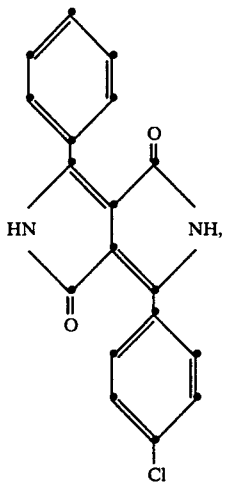
(XII)

which colours PVC red.

Analysis: C₁₈H₁₁N₂O₂Cl: MG 322.5: cal.: C 66.99%; H 3.44%; N 8.68%; Cl 10.99%; found: C 66.50%; H 3.63%; N 8.54%; Cl 10.40%

λ$_{max}$ (nm) measured in dimethylformamide: 471/504

EXAMPLES 5 TO 8

Following the procedure of Example 4, further pigments of the formula

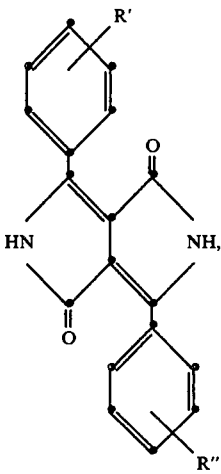

are obtained, wherein R' and R" have the meanings given in the following table.

| Example | R' | R" | Colour in PVC | λ$_{max}$ (nm) measured in dimethylformamide |
|---|---|---|---|---|
| 5 | p-CN | H | red | 470/504 |
| 6 | p-CH₃ | H | red | 470/505 |
| 7 | p-CH₃ | p-CN | red | 498/520 |
| 8 | p-Cl | p-CN | red | 488/520 |

EXAMPLE 9

7.2 g of activated zinc prepared according to Example 2 are suspended in 25 ml of benzonitrile and reacted under nitrogen overnight at 65° C. with 8.75 ml of methyl chloroacetate. ¹H-NMR analysis of the reaction solution shows 40% reaction to the salt of formula XIII

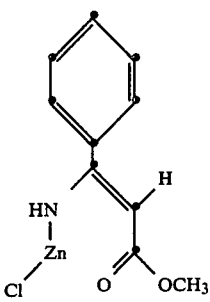
(XIII)

25 ml of xylene and 8.75 ml of methyl chloroacetate are added and the mixture is reacted for 7 hours at reflux temperature. Working up as in Example 2 yields 1.4 g (10% of theory, based on the salt of formula XIII) of the pigment of formula X.

What is claimed is:

1. A process for the preparation of a 1,4-diketopyrrolo-[3,4-c]pyrrole of the formula

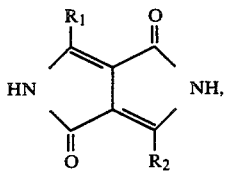

(I)

wherein each of $R_1$ and $R_2$ independently of the other is phenyl of said phenyl substituted by one or two fluorine, chlorine or bromine atoms or mixtures thereof, by one, two or three methoxy or methyl groups or mixtures thereof with chlorine atoms, by cyano, by dimethylamino, by trifluoromethyl, by alkoxycarbonyl of 2 to 3 carbon atoms, by tert-butyl, by cyanophenyl, by acetyl or by alkylbenzoyloxy of 11-14 carbon atoms; biphenylyl; naphthyl or said naphthyl substituted by methoxy; anthryl; phenanthryl; pyridyl or said pyridyl substituted by methyl or by amyloxy; quinolyl; furyl or thienyl, which consists essentially of reacting 1 mole of the compound of the formula

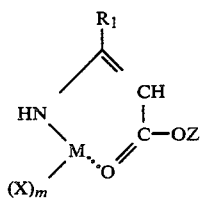

(II)

wherein M is a metal atom, Z is alkyl or aryl, X is halogen or acetate, and m is a value from 0 to 2, with 1 mole of a compound of the formula $YCH_2COOZ$ (III)

wherein Y is halogen, and with 1 mole of a nitrile of the formula $R_1$—CN (IV)

or $R_2$—CN (V)

in an organic solvent and at elevated temperature of 60°-160° C., and isolating the compound of formula I.

2. The process of claim 1, wherein $R_1$ is phenyl or naphthyl or said substituted phenyl or naphthyl substituted by methoxy.

3. The process of claim 1, wherein $R_1$ is phenyl p-chlorophenyl, p-methylphenyl or p-cyanophenyl.

4. A process according to claim 1 utilizing a compound of the formula II, wherein X is bromine, M is zinc, m is 1 and Z is $C_1$-$C_5$alkyl.

5. A process according to claim 1 utilizing a compound of the formula III, wherein Y is bromine and Z is $C_1$-$C_5$alkyl.

6. A process according to claim 1, wherein the starting materials are compounds of the formulae II and V, wherein $R_1$ and $R_2$ are different.

7. A process according to claim 1, wherein the organic solvent is an ether or an aromatic hydrocarbon.

8. A process according to claim 1, wherein the solvent is the nitrile of the formula IV or V.

* * * * *